United States Patent
Fasula et al.

(10) Patent No.: US 9,155,549 B2
(45) Date of Patent: Oct. 13, 2015

(54) HYDROPHOBICALLY MODIFIED ALKALI SOLUBLE EMULSION COMPOSITION WITH POLYMERIC BEADS

(71) Applicant: Rohm and Haas Company, Philadelphia, PA (US)

(72) Inventors: Adam Fasula, Lansdale, PA (US); Kenneth Lennon, Quakertown, PA (US); Partha S. Majumdar, Lansdale, PA (US); Edwin Hugh Nungesser, Horsham, PA (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/040,947

(22) Filed: Sep. 30, 2013

(65) Prior Publication Data

US 2014/0114012 A1    Apr. 24, 2014

Related U.S. Application Data

(60) Provisional application No. 61/706,925, filed on Sep. 28, 2012.

(51) Int. Cl.
| | |
|---|---|
| *C09D 133/06* | (2006.01) |
| *A61B 17/17* | (2006.01) |
| *C09D 133/08* | (2006.01) |
| *A61B 17/14* | (2006.01) |
| *A61B 17/16* | (2006.01) |

(52) U.S. Cl.
CPC ........... *A61B 17/1764* (2013.01); *A61B 17/141* (2013.01); *A61B 17/1655* (2013.01); *C09D 133/08* (2013.01); *C08L 2201/54* (2013.01)

(58) Field of Classification Search
CPC .............. C09D 133/08; C08L 2201/54; A61B 17/141; A61B 17/1764
USPC .................................................. 524/502, 523
See application file for complete search history.

(56) References Cited

U.S. PATENT DOCUMENTS

| | | | |
|---|---|---|---|
| 4,055,607 A | 10/1977 | Sullivan et al. | |
| 4,059,552 A | 11/1977 | Zweigle et al. | |
| 4,403,003 A | 9/1983 | Backhouse | |
| 4,461,849 A | 7/1984 | Karickhoff | |
| 4,518,724 A | 5/1985 | Kuwajima et al. | |
| 4,717,620 A | 1/1988 | Bowen et al. | |
| 5,237,004 A | 8/1993 | Wu et al. | |
| 5,910,529 A | 6/1999 | Wollner | |
| 6,649,687 B1 | 11/2003 | Gheewala et al. | |
| 7,829,626 B2 | 11/2010 | Chiou et al. | |
| 2007/0043159 A1* | 2/2007 | Bardman et al. | 524/501 |
| 2007/0292677 A1 | 12/2007 | Kayima et al. | |
| 2012/0115999 A1* | 5/2012 | Peera et al. | 524/249 |
| 2013/0053499 A1 | 2/2013 | Donovan et al. | |

FOREIGN PATENT DOCUMENTS

| | | | |
|---|---|---|---|
| EP | 522454 A1 | | 1/1993 |
| EP | 0622402 A1 | | 11/1994 |
| EP | 1236777 A1 | | 9/2002 |
| EP | 1754729 A1 | | 2/2007 |
| EP | 1754730 | * | 2/2007 |
| EP | 1754730 A1 | | 2/2007 |
| EP | 2182033 A1 | | 5/2010 |
| EP | 2586835 | * | 1/2013 |
| EP | 2586835 A1 | | 5/2013 |
| GB | 1572837 A | | 8/1980 |
| WO | 0136558 A2 | | 5/2001 |

* cited by examiner

*Primary Examiner* — James J Seidleck
*Assistant Examiner* — Deve E Valdez
(74) *Attorney, Agent, or Firm* — Reid S. Willis

(57) ABSTRACT

The present invention relates to a composition comprising an aqueous dispersion of a film-forming polymer, spherical polymer beads, a HASE rheology modifier, and optionally a pigment. The composition is useful in coatings compositions.

8 Claims, No Drawings

HYDROPHOBICALLY MODIFIED ALKALI SOLUBLE EMULSION COMPOSITION WITH POLYMERIC BEADS

BACKGROUND OF THE INVENTION

The present invention relates to a composition comprising a binder, a hydrophobically modified alkali soluble emulsion (HASE) thickener, and spherical polymeric beads.

Decorative wall coatings optimally require a flawless finish, an ambitious undertaking because of commonly occurring defects on the surface of the coating. These defects often require tedious repainting of the surface, and delivering a finish that is free of brush marks, paint overlap, and surface irregularity remains a challenge for even the most skilled painter.

Two common problems associated with fixing defects are poor touch-up and flashing: Poor touch-up refers to a noticeable difference in the overall final appearance of a repainted surface with respect to the originally painted surface. Flashing—a term coined by professional painters—manifests itself in the form of relatively bright spots that fleetingly appear on a wall when light strikes the wall's surface at certain angles. Fixing these defects require special efforts, sometimes to no avail.

Accordingly, it would be desirable to find a formulation that results in acceptable touch-up and flash properties while maintaining other essential properties of the formulation.

SUMMARY OF THE PRESENT INVENTION

The present invention addresses a need in the art by providing a composition comprising an aqueous dispersion of:
a) a film-forming polymer having a volume average diameter in the range of from 50 nm to 300 nm;
b) spherical polymer beads having a volume average diameter in the range of from 0.8 µm to 20 µm; and
c) a HASE rheology modifier having a backbone with pendant alkylated ethoxylate groups, wherein the alkylated portion of the alkylated ethoxylate groups has a Hansch parameter in the range of from 4 to 7.5;
the weight-to-weight ratio of the spherical beads to the film-forming polymer is in the range of from 90:10 to 10:90;
the weight-to-weight ratio of the HASE rheology modifier to the film-forming binder is in the range of 2 to 25; and
the concentration of pendant alkylated ethoxylate groups is from 1 to 20 weight percent, based on the solid weight of the HASE rheology modifier.

The composition of the present invention addresses a need in the art by providing a formulation with acceptable touch-up and flash properties, as well as acceptable KU stability.

DETAILED DESCRIPTION OF THE INVENTION

The present invention addresses a need in the art by providing a composition comprising an aqueous dispersion of:
a) a film-forming polymer having a volume average diameter in the range of from 50 nm to 300 nm;
b) spherical polymer beads having a volume average diameter in the range of from 0.8 µm to 20 µm; and
c) a HASE rheology modifier having a backbone with pendant alkylated ethoxylate groups, wherein the alkylated portion of the alkylated ethoxylate groups has a Hansch parameter in the range of from 4 to 7.5;
the weight-to-weight ratio of the spherical beads to the film-forming polymer is in the range of from 90:10 to 10:90;
the weight-to-weight ratio of the HASE rheology modifier to the film-forming binder is in the range of 2 to 25; and
the concentration of pendant alkylated ethoxylate groups is from 1 to 20 weight percent, based on the solid weight of the HASE rheology modifier.

The film-forming polymer preferably has a $T_g$ in the range of from −60° C. to 80° C.

Examples of suitable film-forming polymers include urethane, olefin, acrylic, styrene-acrylic, vinyl ester-ethylene (including vinyl acetate-ethylene and vinyl versatate-ethylene), vinyl ester-acrylic (including vinyl acetate-acrylic and vinyl versatate-acrylic), silicone, vinylidene halide, and vinyl halide polymers.

The aqueous composition further includes substantially spherical polymer beads having a preferred volume average diameter in the range of 0.85 µm to 10 µm. The spherical beads are advantageously used as a replacement for traditional inorganic extenders, which typically have high aspect ratios. Although the composition may include extenders, it is preferred that extenders generally be limited or excluded altogether.

The spherical beads are organic and may be prepared by any of a number of method known in the art, including emulsion polymerization, seeded growth, and suspension polymerization processes. The spherical beads may be prepared in a single stage process or in a multiple step process. Examples of suitable polymers for the spherical beads include polyacrylates, polymethacrylates, polystyrenes, polyacrylamides, polyurethanes, polysiloxanes, polyolefins, polyacrylonitrile, nylons, poly(vinyl esters) (including poly(vinyl acetate) and poly(vinyl versatates)), poly(vinyl halides), and poly(vinylidene halides), and combinations thereof, and copolymers thereof. The spherical polymer beads are preferably crosslinked with a suitable crosslinking group such as allyl methacrylate or divinyl benzene. Preferably at least 60% of the polymeric beads have a diameter in the range of 0.85 to 20 µm; more preferably, at least 80% of the polymeric beads have a diameter in the range of 1 to 10 µm.

Examples of preferred monomers that can be used to prepare the spherical beads include methyl methacrylate, ethyl acrylate, butyl acrylate, ethylhexyl acrylate, styrene, and α-methyl styrene, and combinations thereof.

The spherical beads are preferably compressible and preferably solid throughout (i.e., preferably not hollow sphere beads). The compressibility of particles can be characterized by their K-values, as disclosed by Kim et al., J. Appl. Polym. Sci., Vol. 104, 2350-2360 (2007). Preferably, the spherical beads have a K-value when measured at 10% compression ($K_{10}$) in the range of from $1 \times 10^{10}$ N/m² to $5 \times 10^{10}$ N/m²; it is further preferable that the spherical beads have a $K_0/K_{10}$ ($K_0$=full compression) of greater than 1.5, more preferably greater than 3 when measured at a compression rate of 7.75 mN/s.

Preferably, the weight-to-weight ratio of the spherical beads to the film-forming polymer is in the range of from 75:25 to 25:75, most preferably from 70:30 to 30:70. A preferred pigment is $TiO_2$. Preferably, the weight-to-weight ratio of pigment to the polymeric beads and the film forming polymer is in the range of from 10:90 to 60:40, more preferably from 15:85 to 50:50.

The composition further comprises a HASE thickener, which preferably includes structural units of a) an acrylate, for example ethyl acrylate, butyl acrylate, or ethylhexyl acrylate, preferably ethyl acrylate; b) an acid, preferably acrylic acid, methacrylic acid, itaconic acid, or phosphoethyl methacrylate, preferably acrylic acid or methacrylic acid; and c) an alkylated ethoxylate monomer, preferably an alkylated ethoxylate acrylate or methacrylate, wherein the alkylated portion (also known as the hydrophobe) is characterized by a Hansch parameter in the range of from 4 to 7.5.

The term "structural unit" is used herein to describe the remnant of the recited monomer after polymerization. An example of a structural unit of a suitable alkylated ethoxylate methacrylate group is illustrated as Structure I:

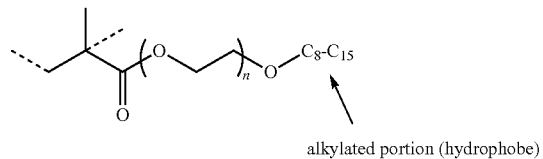

alkylated portion (hydrophobe)

where n is in the range of from 10 to 50, more preferably from 15 to 30, most preferably from 18 to 24, and where the dotted lines represent the attachment of the pendant group to the polymer backbone. An example of a suitable alkylated ethoxylate methacrylate monomer is $C_{12}H_{25}(EO)_{23}$ methacrylate.

Preferably, at least 90%, of the alkylated portion comprises $C_{10}$-$C_{15}$-alkyl groups; more preferably, at least 95% of the alkylated portion comprises $C_{10}$-$C_{15}$-alkyl groups; most preferably, at least 95% of the alkylated portion comprises linear $C_{12}$-$C_{14}$-alkyl groups. The weight-to-weight ratio of the HASE rheology modifier to the film-forming polymer is preferably in the range of from 5, more preferably from 7, to 20, more preferably to 17.

Preferably, the HASE thickeners contain, based on the solid weight of the HASE, from about 40 to 60 w/w % structural units of ethyl acrylate, from 35 to 50 w/w % structural units of methacrylic acid, and from 1 to 10 w/w % structural units of pendant alkylated ethoxylate groups.

The composition of the present invention can be conveniently prepared by combining together a stable aqueous dispersion of the film-forming polymer (also known as a binder or a latex binder), an aqueous dispersion of the polymeric beads, and the HASE, either as an aqueous emulsion or as a solution (as disclosed in U.S. Pat. No. 6,063,857). The composition preferably includes a pigment, which may be a whitening pigment such as $TiO_2$ or a non-white pigment (a colorant). The $TiO_2$ can be added as a solid, as a dispersion, or as a slurry. The composition of the present invention may further include any or all of the following materials: Solvents; fillers; dispersants; surfactants; defoamers; coalescents; colorants; preservatives; flow agents; leveling agents; and neutralizing agents. The composition is especially useful for colored paints where colorant is added at the site of sale of the paint.

The composition of the present invention can be used to prepare coatings formulations with improved touch-up and flash properties, as well as improved KU stability.

EXAMPLES

The following examples are for illustrative purposes only and are not intended to limit the scope of the invention. The materials used in coating formulations are described in Table 1. All of the HASEs contain polymerized units of ethyl acrylate and methacrylic acid. HASEs 1, 2, and 3 contain a $C_{12}$-$C_{14}$ hydrophobe; HASEs 4 and 5 contain a $C_{16}$-$C_{18}$ hydrophobe; and HASE 6 contains a 3:1 w/w mixture of a $C_{16}$-$C_{18}$ hydrophobe and a $C_{12}$-$C_{14}$ hydrophobe.

TABLE 1

List of the materials and Abbreviations

| | |
|---|---|
| RHOPLEX ™ VSR-50 Acrylic Binder | Acrylic Binder |
| 5.0-µm gradient acrylic bead | Beads |
| Laponite RD Synthetic layered silicate | Clay |
| BYK-028 Silicone defoamer | Defoamer |
| Texanol Ester alcohol | Coalescent |
| ACRYSOL ™ RM-2020 HEUR Thickener | RM-2020 |
| ACRYSOL ™ DR-6600 Thickener | HASE 1 |
| ACRYSOL ™ DR-5500 Thickener | HASE 2 |
| ACRYSOL ™ RM-7 Thickener | HASE 3 |
| ACRYSOL TT-615 Thickener | HASE 4 |
| ACRYSOL DR-72 Thickener | HASE 5 |
| ACRYSOL TT-935 Thickener | HASE 6 |
| Natrosol 250 HBR Thickener | HEC |
| ACRYSOL ™ ASE-60 Copolymer | ASE |
| ACRYSOL ™ RM-8W HEUR Thickener | 8W-HEUR |
| Red Iron Oxide F888-1045 Colorant | Iron Oxide solution |

RHOPLEX ™ and ACRYSOL ™ are Trademarks of The Dow Chemical Company or Its Affiliates.

Aqueous solutions (3.0 weight %) of Clay and the HEC Thickener were prepared separately using an overhead stirrer. Clay solution was consumed within 12 h after preparation.

Intermediate 1:

Preparation of 5-µm Polymer Beads

A. Preparation of Pre-Seed

Three separate mixtures were prepared, a first mixture (Mixture A) containing sodium carbonate (0.38 g) in water (208 g), a second mixture (Mixture B), containing butyl acrylate (98 g), butylene glycol diacrylate (0.25 g), allyl methacrylate (2.0 g), and sodium dodecylbenzenesulfonate (4.0 g, 10% aq.) and a third mixture (Mixture C) containing potassium persulfate (0.063 g) in water (35 g). A reactor equipped with a stirrer and condenser and blanketed with $N_2$ was charged with Mixture A and heated to 82° C., after which time 15% of Mixture B and 25% of Mixture C were added to the reactor. The reaction mixture was stirred for 1 h, after which the remaining portions of Mixture B and Mixture C were metered into the reactor over 90 min. Stirring was continued at 82° C. for 2 h, after which the reactor contents were cooled to room temperature. The average diameter of the resulting emulsion particles was found to be 0.2 micron, as measured by light scattering using a BI-90 Plus instrument from Brookhaven Instruments Company, 750 Blue Point Road, Holtsville, N.Y. 11742.

B. Preparation of Oligomer Seed

1. Preparation of n-Dodecylmercaptan (n-DDM) Emulsion

DI water (1236.7 g) was charged into a vessel followed by sodium dodecylbenzenesulfonate (42.20 g, 23% active) then n-DDM (1067.4 g). The mixture was agitated with a high speed mixer.

2. Kettle Preparation

A kettle was charged with water (7425.0 g), heated with stirring to 88-90° C. and sparged with $N_2$ for 30 min. The following solutions were then added to the kettle: (a) a solution of 50% methyl-β-cyclodextrin (97.7 g) and DI water (45.0 g); (b) a solution of ammonium persulfate (4.9 g) and DI water (100.0 g); and (c) seed containing 266.4 g of Intermediate 1A and DI water (315.0 g). With the kettle temperature maintained at 83-87° C., a mixture of stable monomer emulsion containing butyl acrylate (3969.0 g), methyl methacrylate (873.0 g), methacrylic acid (9.9 g), sodium dodecyl benzenesulfonate (86.0 g, 23% active), DI water (1075.5 g) and a solution containing sodium carbonate (3.9 g) and DI water (135.0 g) were fed over 240 min. The n-DDM emulsion was fed over 235 minutes. The co-feed catalyst solution containing ammonium persulfate (9.9 g) and DI water (450 g) was fed over 240 min. After completion of addition of the n-DDM emulsion, DI water (225.0 g) was fed to rinse over 5 min. When the addition of monomer emulsion and co-feed catalyst were complete, water rinses (180.0 g and 45.0 g) were carried out to rinse monomer emulsion and co-feed catalyst, respectively. The reactor was maintained at 83-87° C. for an additional 15 min and then cooled to 70° C. Next, a solution of FeSO$_4$.7H$_2$O (0.26 g), VERSENE™ Chelating Agent (A Trademark of The Dow Chemical Company or its Affiliates, 0.36 g), and DI water (70.7 g), were added to the reactor and held for 15 min. Three chaser solutions were prepared separately. Each chaser solution containing a catalyst part (ammonium persulfate (1.53 g) in DI water (93.2 g)) and an activator part (sodium sulfoxylate formaldehyde (0.95 g) in DI water (93.2 g)). The catalyst and activator parts of each chase were added to the reactor separately and each held for 15 min at 70° C. The reaction mixture was then cooled to 40° C., whereupon an inhibitor solution containing 5 wt. % of 4-hydroxy TEMPO in DI water was added a level of 0.034 wt. % based on monomer. Finally, the reaction mixture was filtered and used without further purification.

C. Preparation of 5-µm Polymer Beads

A reactor was charged with water (7618.0 g) and heated to 78° C. A monomer emulsion containing butyl acrylate (5113.0 g), α-methylstyrene (26.8 g), allyl methacrylate (214.2 g), sodium dodecylbenzensulfonate (80.8 g, 23% active), and DI water (2201.9 g) was prepared separately. Seed containing Intermediate 1B (66.5 g) and water (146.3 g) was added to the reactor under agitation. The monomer emulsion was fed to the reactor at a rate of 116.43 g/min and the temperature maintained at above 65° C. Monomer emulsion feed was stopped after the addition a portion of the emulsion (1510.0 g). The reaction was continued for 30 min and then cooled to 65° C. Initiator emulsion, containing sodium dodecylbenzensulfonate (1.10 g, 23% active), t-butyl per-2-ethylhexanoate (24.44 g, 97% active), and DI water (151.2 g), was prepared separately. Initiator emulsion was added to the reactor and the exotherm was monitored. After peak exotherm, the temperature of the reaction mixture was increased to 83° C. over 10 min. The remaining monomer emulsion was added to the reactor a rate of 116.43 g/min. After completion of monomer emulsion addition the reactor was cooled 78° C. Three solutions (stage II promoter, co-feed catalyst and co-feed activator) were prepared separately. Stage II promoter contained FeSO$_4$.7H$_2$O (0.04 g) and chelating agent (0.02 g) in DI water (26.61 g). The co-feed catalyst contained t-butyl hydroperoxide (7.02 g, 70% active) in water (524.5 g). The co-feed activator was a solution of isoascorbic acid (3.58 g) in water (524.5 g). Stage II promoter was added to the reactor. Next, the co-feed catalyst and the co-feed activator were added separately at a rate of 9.5 g/min over 50 min. A second monomer emulsion containing methyl methacrylate (1229.0 g), EA (53.17 g), sodium dodecylbenzensulfonate (16.15 g, 23%), and water (419.25 g) was to the reactor at a rate of 37.7 g/min over 45 min. The temperature of the reaction was maintained at 78° C. After completion of the second monomer emulsion addition, the reactor was cooled to 65° C., whereupon the chaser catalyst and activator solutions were added separately at a rate of 8.60 g/min over 40 min. The chaser catalyst was a solution of t-butyl hydroperoxide (9.26 g, 70% active) in DI water (394.5 g). The chaser activator solution contained isoascorbic acid (4.68 g) in DI water (394.5 g). After chaser catalyst and activator solutions addition, the reactor was cooled to 25° C. and the solution filtered.

Particle Size Measurement

Mean particle size was measured using a Disc Centrifuge Photosedimentometer ("DCP") (CPS Instruments, Inc.) that separates modes by centrifugation and sedimentation through a sucrose gradient. The samples were prepared by adding 1-2 drops into DI water (10 mL) containing 0.1% sodium lauryl sulfate. About 0.1 mL of the sample was injected into the spinning disc filled with 15 mL sucrose gradient. Samples were analyzed relative to a polystyrene calibration standard. Specific conditions were: sucrose gradient: 2-8%; disc speed: 10,000 rpm; calibration standard: 895 nm diameter polystyrene. The mean particle size was found to be 4.25 µm.

Examples 2-4 and Comparative Examples 1-6

Preparation of Samples

The procedure for preparing the formulations of Examples 2-4 and Comparatives 1-6 was substantially as described in Example 1. The actual amounts used in each example and comparative example (in grams) are shown in Tables 2 and 3.

TABLE 2

Composition of Formulations Containing HASE, HEC, ASE, and HEUR Thickeners

| Ingredients | Example 1 | Comparative 1 | Comparative 2 | Comparative 3 |
|---|---|---|---|---|
| Mixing Stage-1 | | | | |
| Beads | 440.79 | 419.83 | 442.26 | 441.47 |
| Laponite RD (3%) | 43.47 | 41.40 | 43.62 | 43.54 |
| Acrylic Binder | 300.38 | 286.09 | 301.38 | 300.84 |
| Defoamer | 0.48 | 0.46 | 0.48 | 0.48 |
| Coalescent | 6.83 | 6.50 | 6.85 | 6.84 |
| AcrysoRM-2020 | 9.68 | 9.22 | 9.71 | 9.69 |
| Mixing Stage-2 | | | | |
| Water | 20.91 | 0.00 | 49.15 | 56.55 |
| HASE1 | 39.55 | 0.00 | 0.00 | 0.00 |
| HEC (3%) | 0.00 | 100.10 | 0.00 | 0.00 |
| ASE | 0.00 | 0.00 | 10.78 | 0.00 |
| 8W-HEUR | 0.00 | 0.00 | 0.00 | 5.35 |
| Ammonia (28%) | 4.2 | 0.17 | 0.90 | 0.00 |
| Total weight (g) | 866.29 | 863.78 | 865.13 | 864.77 |

TABLE 3

Compositional of Formulations Containing Different HASE Thickeners

| Ingredients | Ex. 2 | Ex. 3 | Ex. 4 | Ex. 5 | Comp. 4 | Comp. 5 | Comp. 6 |
|---|---|---|---|---|---|---|---|
| Mixing Stage-1 | | | | | | | |
| Beads | 220.40 | 220.40 | 220.40 | 220.40 | 220.40 | 220.40 | 220.40 |
| Acrylic Binder | 150.20 | 150.20 | 150.20 | 150.20 | 150.20 | 150.20 | 150.20 |
| BYK-028 | 0.24 | 0.24 | 0.24 | 0.24 | 0.24 | 0.24 | 0.24 |
| Texanol | 3.42 | 3.42 | 3.42 | 3.42 | 3.42 | 3.42 | 3.42 |
| RM-2020 | 4.84 | 0.00 | 0.00 | 0.00 | 0.00 | 0.00 | 0.00 |

TABLE 3-continued

Compositional of Formulations Containing Different HASE Thickeners

| Ingredients | Ex. 2 | Ex. 3 | Ex. 4 | Ex. 5 | Comp. 4 | Comp. 5 | Comp. 6 |
|---|---|---|---|---|---|---|---|
| Mixing Stage-2 | | | | | | | |
| Water | 25.35 | 26.69 | 18.79 | 40.6 | 53.55 | 56.67 | 52.21 |
| HASE1 | 25.70 | 29.06 | 0.00 | 0.00 | 0.00 | 0.00 | 0.00 |
| HASE2 | 0.00 | 0.00 | 36.83 | 0.00 | 0.00 | 0.00 | 0.00 |
| HASE3 | 0.00 | 0.00 | 0.00 | 16.77 | 0.00 | 0.00 | 0.00 |
| HASE4 | 0.00 | 0.00 | 0.00 | 0.00 | 4.77 | 0.00 | 0.00 |
| HASE5 | 0.00 | 0.00 | 0.00 | 0.00 | 0.00 | 5.44 | 0.00 |
| HASE6 | 0.00 | 0.00 | 0.00 | 0.00 | 0.00 | 0.00 | 5.75 |
| $NH_3$ (28%) | 2.85 | 2.99 | 4.04 | 1.37 | 0.63 | 0.65 | 0.78 |
| Total (g) | 433.00 | 433.00 | 433.92 | 433.00 | 433.21 | 437.02 | 433.00 |

Test Methods.

The following test methods were used to characterize the coatings.

Touch-Up and Flashing.

First, the experimental coating was applied to a wall covered with a commercial primer, using a 1.5" Wooster® Golden Glo Brush to draw a first "X" at the middle on the left side of the wall. After 1 h, the wall was painted with the experimental coating using a Sherwin Williams contractor series 9" roller. After drying for 4 h, a second "X" was drawn at the center of the wall with the experimental coating. After drying for 1 h, a second coat of the experimental coating was applied to the wall using a roller and allowed to dry overnight. Finally, a third "X" was drawn at the middle on the right side of the wall using the experimental coating. Touch up and flashing were evaluated after 6 h of drying of the third "X" mark. Touch up was evaluated by the naked eyes under an incandescent light source or under normal daylight. Flashing was evaluated under dark using a LED light source. The ranking describing the appearance of coating are listed in Table 4, with 1 being the worst and 5 the best.

TABLE 4

Ranking Used to Evaluate Touch-up and Flashing Properties of Coatings

| Rank | Touch up | Flashing |
|---|---|---|
| 1 | Visible brush mark from third "X" at 0° viewing angle (perpendicular) from wall. | Both "X" marks were visible at any viewing angle. |
| 2 | Visible brush mark from third "X" between 0° to 30° viewing angle. | Second "X" mark was visible and first "X" mark was hardly visible at any viewing angle. |
| 3 | Visible brush mark from third "X" between 30° to 45° viewing angle. | Second "X" mark was visible but first "X" mark was not visible at any viewing angle. |
| 4 | Visible brush mark from third "X" between 45° to 60° viewing angle | Second "X" mark was hardly visible but first "X" mark was not visible at any viewing angle. |
| 5 | No visible brush mark from third "X" at any viewing angle (from 0° to 90°). | First and second "X" marks were not visible at any viewing angle. |

Liquid paints were characterized using ICI and Stormer viscosity. ICI viscosity was measured following the procedure described in ASTM D3205. The results were reported in poise (P). ASTM D562 was followed to measure Stormer viscosity. The results were reported in Krebs Units (KU).

Table 5 describes touch up, flashing, and viscosity of the experimental and comparative coatings. Example 1 exhibited a combination of good touch up (rating 3 to 5) and flashing (rating 3 to 5) properties with a Stormer viscosity of ~100 KU. Comparatives 1 and 2 showed good touch up and flashing but had very low Stormer and ICI viscosities. Paints with very low Stormer and ICI viscosities could have significant problems such as settling of pigments in can, spattering during application etc. Comparative 3 had very poor touch up and flashing properties along with very low Stormer and ICI viscosities.

Table 6 compares the drop in Stormer viscosity due to colorant addition in coatings containing different HASE thickeners. Examples 2-5, which showed less than a 20-unit drop in Stormer viscosity due to colorant addition contain HASE thickeners with 2-10 wt. % short hydrophobic units ($C_{12}$-$C_{14}$). However, Comparatives 4-6 which showed greater than a 25-unit drop in Stormer viscosity due to colorant addition contain HASE thickeners with either 5-10 wt. % long hydrophobic units ($C_{16}$-$C_{18}$) or a mixture of short (1.25 wt. %) and long (3.75 wt. %) hydrophobic units. $KU_o$ refers to Stormer viscosity before colorant addition, $KU_f$ refers to Stormer viscosity after colorant addition, and $\Delta KU$ refers to $KU_f$-$KU_o$.

TABLE 5

Properties of the coatings described in Table 1

| Properties | Ex. 1 | Comp. 1 | Comp. 2 | Comp. 3 |
|---|---|---|---|---|
| Touch up | 3 | 5 | 5 | 1 |
| Flashing | 5 | 3 | 2 | 2 |
| Stormer viscosity (KU) | 102.0 | 76.8 | 75.0 | 66.3 |
| ICI viscosity (P) | 2.4 | 0.6 | 0.6 | 0.45 |

TABLE 6

Properties of the coatings described in Table 2

| Properties | Ex. 2 | Ex. 3 | Ex. 4 | Ex. 5 | Comp. 4 | Comp. 5 | Comp. 6 |
|---|---|---|---|---|---|---|---|
| $KU_o$ | 105.7 | 107.2 | 112.2 | 115.3 | 111.4 | 120.1 | 119.8 |
| $KU_f$ | 103.9 | 104 | 107.5 | 99.5 | 84.4 | 81.3 | 72.4 |
| $\Delta KU$ | -1.8 | -3.2 | -4.7 | -15.8 | -27 | -38.8 | -47.4 |

The data from Table 5 show that only the compositions containing the HASE rheology modifiers achieved acceptable touch-up, flash, and KU viscosity stability. Table 6 shows the importance of choosing a hydrophobe of the proper length. It has surprisingly been discovered that the difference between a $C_{12}$-$C_{14}$-alkyl group hydrophobe and a $C_{16}$-$C_{18}$- alkyl group results in a significant difference in KU stability. Though not bound by theory, it is believed that the HASE thickeners with $C_{16}$-$C_{18}$ phobes show KU instability because relatively small amounts of these HASEs are required to achieve the initial target viscosity. However, when materials such as colorants are added to formulation, the demand for rheology modifier increases. Consequently, the amount of rheology modifier originally added to the paint becomes insufficient, resulting in a formulation exhibiting KU instability. On the other hand, when a HASE with a lower Hansch parameter hydrophobe is used (less than 7.5), the requirement for the amount of thickener to achieve the initial target viscosity is much higher. Although this increased initial loading makes this HASE less efficient, it is nevertheless more effective; once the colorant is added, the increase in demand has already been met resulting in a KU stable formulation.

Table 7 shows the correlation between Hansch parameters and alkyl chain length. The calculations were carried using US EPA Kowwin software. Using the Simplified Molecular Input Line Entry System (SMILES), the Hansch parameter for a particular group is calculated by first calculating the Log $K_{ow}$ of an alkane having one more methyl group than the alkyl group of interest, then subtracting certain fragment constants. For example, to calculate the Hansch parameter of an n-$C_{12}H_{25}$ group, one first calculates the $K_{ow}$ for n-$C_{13}$—$H_{28}$, which is 6.73. One then subtracts the fragment constant for one of the methyl groups (0.55) as well as the equation constant (0.23) to arrive at a Hansch parameter of 5.9 for n-$C_{12}H_{25}$.

TABLE 7

Calculated Hansch Parameters for Linear $C_8$-$C_{18}$- Alkyl Groups

| Linear alkyl chain length | Hansch Parameter |
| --- | --- |
| 8 | 4.0 |
| 9 | 4.5 |
| 10 | 5.0 |
| 11 | 5.5 |
| 12 | 5.9 |
| 13 | 6.4 |
| 14 | 6.9 |
| 15 | 7.4 |
| 16 | 7.9 |
| 17 | 8.4 |
| 18 | 8.9 |

The invention claimed is:

1. A composition comprising an aqueous dispersion of:
 a) a film-forming polymer having a volume average diameter in the range of from 50 nm to 300 nm;
 b) spherical polymer beads having a volume average diameter in the range of from 0.8 µm to 20 µm; and
 c) a HASE rheology modifier having a backbone with pendant alkylated ethoxylate groups, wherein the alkylated portion of the alkylated ethoxylate groups has a Hansch parameter in the range of from 4 to 7.5;
 the weight-to-weight ratio of the spherical beads to the film-forming polymer is in the range of from 90:10 to 10:90;
 the weight-to-weight ratio of the HASE rheology modifier to the film-forming polymer is in the range of 2 to 25; and
 the concentration of pendant alkylated ethoxylate groups is from 1 to 20 weight percent, based on the solid weight of the HASE rheology modifier.

2. The composition of claim 1 wherein the film-forming polymer is an acrylic, styrene-acrylic, vinyl acetate-ethylene, or vinyl acetate-acrylic polymer having a $T_g$ in the range of −60° C. and 80° C.; and the composition further includes a pigment, wherein the weight-to-weight ratio of the pigment to the polymeric beads and the film forming polymer is in the range of from 0.5:99.5 to 70:30.

3. The composition of claim 2 wherein at least 90% of the alkylated portion of the alkylated ethoxylate groups comprise $C_{10}$-$C_{15}$-alkyl groups; wherein the spherical beads have a volume average diameter in the range of 0.85 µm and 10 µm; wherein
 the weight-to-weight ratio of the spherical beads to the film-forming polymer is in the range of from 75:25 to 25:75;
 the weight-to-weight ratio of the HASE rheology modifier to the film-forming polymer is in the range of from 5 to 20;
 the weight-to-weight ratio of pigment to the polymeric beads and the film forming polymer is in the range of from 10:90 to 60:40, wherein the pigment is $TiO_2$ or a non-white colorant, or a combination thereof.

4. The composition of claim 1 wherein the spherical polymer beads are solid throughout and comprise structural units of one or more monomers selected from the group consisting of methyl methacrylate, ethyl acrylate, butyl acrylate, ethylhexyl acrylate, styrene, α-methyl styrene; and wherein the spherical polymer beads have a $K_{10}$ value in the range of from $1\times10^{10}$ N/m$^2$ to $5\times10^{10}$ N/m$^2$.

5. The composition of claim 1 wherein at least 95% of the alkylated portion of the alkylated ethoxylate groups comprises linear $C_{12}$-$C_{14}$-alkyl groups; and wherein the spherical beads have a $K_0/K_{10}$ of greater than 3 when measured at a compression rate of 7.75 mN/s; and wherein at least 80% of the polymeric beads have a diameter in the range of 1 to 10 µm.

6. A method comprising combining together a stable aqueous dispersion of a film-forming polymer, an aqueous dispersion of spherical polymeric beads, and an aqueous solution or emulsion of a HASE rheology modifier, wherein
 the HASE rheology modifier has a backbone with pendant alkylated ethoxylate groups;
 the alkylated portion of the alkylated ethoxylate groups has a Hansch parameter in the range of from 4 to 7.5;
 wherein the weight-to-weight ratio of the spherical beads to the film-forming polymer is in the range of from 90:10 to 10:90;
 the weight-to-weight ratio of the HASE rheology modifier to the film-forming binder is in the range of 2 to 25; and
 the concentration of pendant alkylated ethoxylate groups is from 1 to 20 weight percent, based on the solid weight of the HASE rheology modifier.

7. The method of claim 6 which further includes the step of adding $TiO_2$ or a non-white pigment or both to the composition.

8. The method of claim 7 wherein the weight-to-weight ratio of the spherical beads to the film-forming polymer is in the range of from 75:25 to 25:75; the weight-to-weight ratio of the $TiO_2$ or non-white pigment or both to the polymeric beads and the film forming polymer is in the range of from 10:90 to 60:40; at least 90% of the alkylated portion of the alkylated ethoxylate groups comprise $C_{10}$-$C_{15}$-alkyl groups; and the spherical beads have a volume average diameter in the range of 0.85 µm and 10 µm.

* * * * *